(12) United States Patent
Onuma

(10) Patent No.: US 10,605,772 B2
(45) Date of Patent: Mar. 31, 2020

(54) ANALYTICAL TOOL AND ANALYTICAL SYSTEM

(71) Applicant: ARKRAY, Inc., Kyoto (JP)

(72) Inventor: Naotsugu Onuma, Kyoto (JP)

(73) Assignee: ARKRAY, Inc., Kyoto (JP)

(*) Notice: Subject to any disclaimer, the term of this patent is extended or adjusted under 35 U.S.C. 154(b) by 221 days.

(21) Appl. No.: 15/152,629

(22) Filed: May 12, 2016

(65) Prior Publication Data
US 2016/0334367 A1    Nov. 17, 2016

(30) Foreign Application Priority Data

May 13, 2015  (JP) .................................. 2015-098354
Apr. 11, 2016  (JP) .................................. 2016-078769

(51) Int. Cl.
*G01N 27/447* (2006.01)
*B01L 3/00* (2006.01)
*G01N 30/60* (2006.01)

(52) U.S. Cl.
CPC ...... *G01N 27/44791* (2013.01); *B01L 3/5027* (2013.01); *G01N 27/44743* (2013.01); *G01N 30/6091* (2013.01); *G01N 30/6095* (2013.01); *B01L 3/502715* (2013.01); *B01L 2200/141* (2013.01); *B01L 2300/044* (2013.01); *B01L 2300/0645* (2013.01); *B01L 2300/0672* (2013.01); *B01L 2300/0874* (2013.01);
(Continued)

(58) Field of Classification Search
None
See application file for complete search history.

(56) References Cited

U.S. PATENT DOCUMENTS 5,955,028 A * 9/1999 Chow ............... B01L 3/502715
                                                      204/600
7,169,277 B2 * 1/2007 Ausserer .......... G01N 27/44743
                                                      204/453
(Continued)

FOREIGN PATENT DOCUMENTS

CN        1455864 A    11/2003
EP       0999443 A2     5/2000
(Continued)

OTHER PUBLICATIONS

Extended European Search Report issued in corresponding European Patent Application No. 16169231.4 dated Oct. 4, 2016.
(Continued)

*Primary Examiner* — Gurpreet Kaur
*Assistant Examiner* — Steven E Rosenwald
(74) *Attorney, Agent, or Firm* — Morgan, Lewis & Bockius LLP

(57) ABSTRACT

An analytical tool for use in analysis of a sample is provided. The analytical tool includes a first unit and a second unit. The first unit has an analysis portion where analysis is performed. The second unit, configured to be coupled with the first unit, has a liquid reservoir for confining a particular liquid used for the analysis of the sample. When the first unit and the second unit are coupled, a fluid passage for conducting the particular liquid from the liquid reservoir into the first unit is formed by only a part of the first unit, or only a part of the second unit, or a combination of respective parts of the first unit and the second unit.

9 Claims, 10 Drawing Sheets

(52) U.S. Cl.
CPC ............ *B01L 2300/0887* (2013.01); *B01L 2400/0415* (2013.01); *B01L 2400/0421* (2013.01); *B01L 2400/0487* (2013.01)

(56) References Cited

U.S. PATENT DOCUMENTS

| | | | |
|---|---|---|---|
| 2001/0008613 A1 | 7/2001 | Kaltenbach et al. | |
| 2002/0033337 A1 | 3/2002 | Ausserer et al. | |
| 2005/0148091 A1* | 7/2005 | Kitaguchi | B01L 3/502715 436/164 |
| 2009/0088336 A1* | 4/2009 | Burd | B01J 19/0046 506/9 |
| 2010/0181199 A1 | 7/2010 | Sugiyama et al. | |
| 2016/0216235 A1 | 7/2016 | Miyata et al. | |

FOREIGN PATENT DOCUMENTS

| | | |
|---|---|---|
| EP | 0999443 A3 | 9/2002 |
| JP | H08-233778 A | 9/1996 |
| JP | 10-148628 A | 6/1998 |
| JP | 11-337521 A | 12/1999 |
| WO | 02/10732 A1 | 2/2002 |
| WO | 2010/010858 A1 | 1/2010 |
| WO | 2015/037308 A1 | 3/2015 |

OTHER PUBLICATIONS

Office Action issued in corresponding Chinese Patent Application No. 201610317645.7 dated Mar. 2, 2018.
Office Action issued in corresponding Chinese Patent Application No. 201610317645.7 dated Nov. 2, 2018.
Office Action issued in corresponding Japanese Patent Application No. 2017-231757 dated Sep. 10, 2019.
Office Action issued in corresponding Japanese Patent Application No. 2016-078769 dated Sep. 10, 2019.
Office Action issued in corresponding Japanese Patent Application No. 2017-231757 dated Nov. 12, 2019.
Office Action issued in related U.S. Appl. No. 15/891,655 dated Feb. 3, 2020.

* cited by examiner

ANALYTICAL TOOL AND ANALYTICAL SYSTEM

BACKGROUND OF THE INVENTION

1. Field of the Invention

The present invention relates to an analytical tool and an analytical system.

2. Description of the Related Art

Various methods for constructing a liquid sample analyzing system have been proposed so far. By such an analyzing system, a sample to be analyzed is applied to an analytical tool, and then the analytical tool is mounted to (e.g., set on, into, etc.) an analytical device for performing required analysis. Some of such analytical systems utilize electrophoresis. JP-A-11-337521, for example, discloses an analysis method that uses an analytical tool having a capillary tube and a spare passage perpendicular to the capillary tube. In this method, the sample retained at the j unction of the capillary tube and the spare passage is subjected to electrophoresis. This method is intended to analyze a very small amount of sample precisely.

In the above conventional method, a dilution liquid and a migration liquid are stored in the main analytical device and introduced into the analytical tool. To the end of this liquid introduction, use may be made of a nozzle for sucking up the stored liquids by an amount necessary for performing the analysis. Then, the nozzle is set to a predetermined portion of the analytical tool, and the diluent or the migration liquid is supplied from the nozzle to the analytical tool.

The analytical tool of the above-noted type may be configured as a disposable, while the nozzle of the analytical device is used repetitively. Thus, the sample liquid used for the previous analysis can remain at the tip of the nozzle after the completion of the previous analysis. Since such nozzle contamination would lead to incorrect results in the subsequent analysis, the nozzle must be cleaned each time the current analysis has been done. However, cleaning of the nozzle is troublesome and will deteriorate the efficiency of the analysis. Moreover, the conventional analytical device needs to have a mechanism for operating the nozzle. This makes the structure of the analytical device complicated and causes an increase in the manufacturing cost. Furthermore, the system employing the large analytical device requires special bottles for storing diluent and migration liquids. To arrange these bottles requires extra room for that, and the system will become unduly bulky and costly. Moreover, since it is necessary to store a large amount of diluent and migration liquids for a plurality of times of analysis, the cost for a single analyzing process will be high.

SUMMARY OF THE INVENTION

The present invention is conceived under the above circumstances, and its object is to provide an analytical tool and an analytical system that enables proper analysis to be conducted while preventing the analytical device from becoming complicated, contaminated or bulky.

According to an aspect of the present invention, there is provided an analytical tool provided with: a first unit including an analysis portion for analyzing a sample; and a second unit configured to be coupled with the first unit and including a liquid reservoir for confining a particular liquid used for the analyzing of the sample. By coupling the first unit and the second unit to each other, a fluid passage is formed for conducting the particular liquid from the liquid reservoir into the first unit. The fluid passage may be provided by only a part of the first unit, or only a part of the second unit, or a combination of respective parts of the first unit and the second unit.

In an embodiment, the second unit may include a sealing member that seals the liquid reservoir and is breakable for forming the fluid passage.

In an embodiment, the first unit may include a sample collecting portion for taking the sample in.

In an embodiment, the sample may be moved in the sample collecting portion by capillary action.

In an embodiment, the analytical tool may be disposable.

In an embodiment, the analytical tool may be configured for use in analysis by electrophoresis, and the analysis portion may be configures as a capillary tube.

In an embodiment, the analytical tool may further include a cylindrical electroconductive member having an inner surface and an outer surface, where the inner surface defines a voltage application passage, and the outer surface is exposed to the outside of the analytical tool.

In an embodiment, the cylindrical electroconductive member may be provided in the second unit.

According to an another aspect of the present invention, there is provided an analytical system utilizing an analytical tool mentioned above and an analytical device to which the analytical tool is mounted.

In an embodiment, the analytical device of the above-mentioned system is configured to perform pressure control for realizing liquid flow relative to the fluid passage.

According to the present invention, the fluid passage formed in the analytical tool in the coupled state is provided by only a part of the first unit, or only a part of the second unit, or a combination of respective parts of the first unit and the second unit. Thus, the introduction of the particular liquid from the second unit into the first unit does not require any additional tool such as a nozzle equipped in the main analytical device. Accordingly, in conducting a required analysis, the main analytical device can be kept out of touch with the particular liquid to be conducted from the second unit to the first unit. As a result, the required analysis can be performed properly without the analytical device having a complicated structure or being contaminated by the particular liquid.

Other features and advantages of the present invention will become clearer from the detailed description given below with reference to the accompanying drawings.

DESCRIPTION OF THE PREFERRED EMBODIMENTS

Preferred embodiments of the present invention are described below with reference to the accompanying drawings.

FIGS. 1-7 show an analytical tool according to a first embodiment of the present invention. The analytical tool A1 of this embodiment includes a first unit 11 and a second unit 12.

Figure 1:
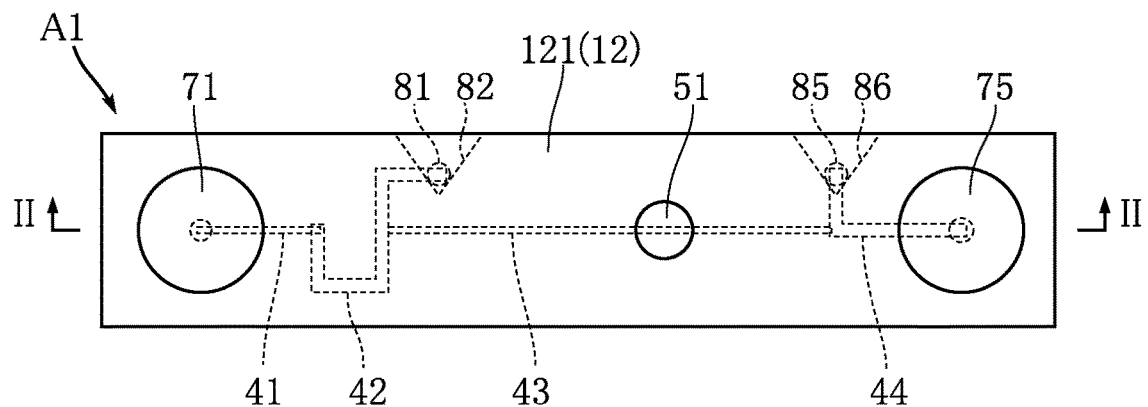
FIG. 1 is a schematic plan view of an analytical tool in a separated state, according to a first embodiment of the present invention.
Figure 2:
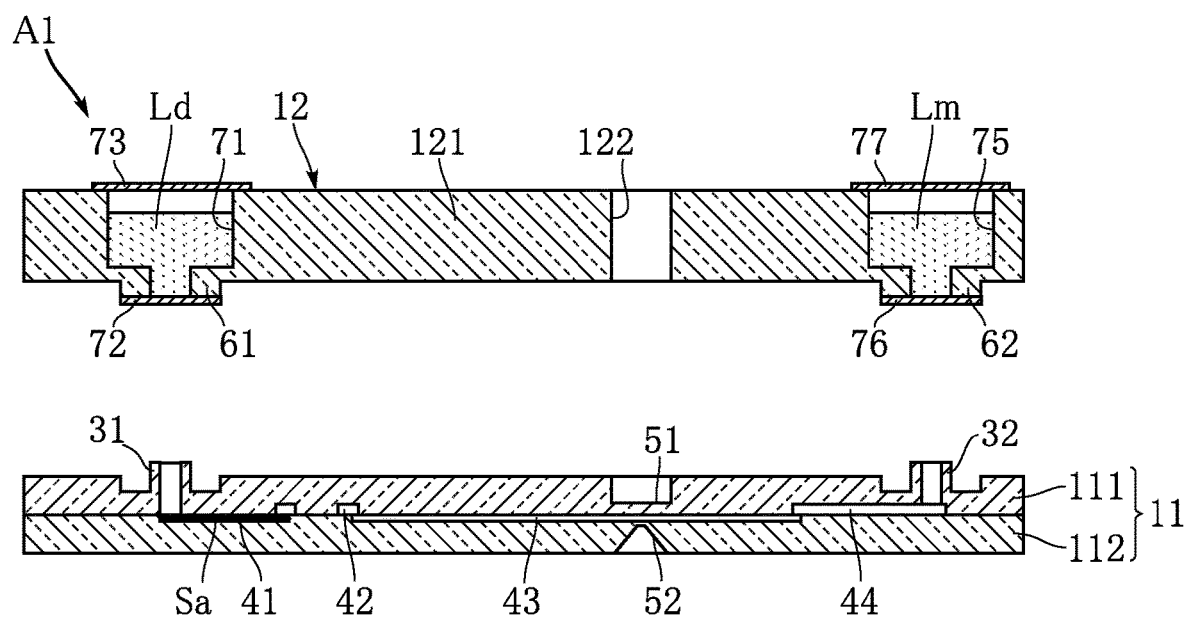
FIG. 2 is a sectional view taken along lines II-II in FIG. 1.
Figure 3:
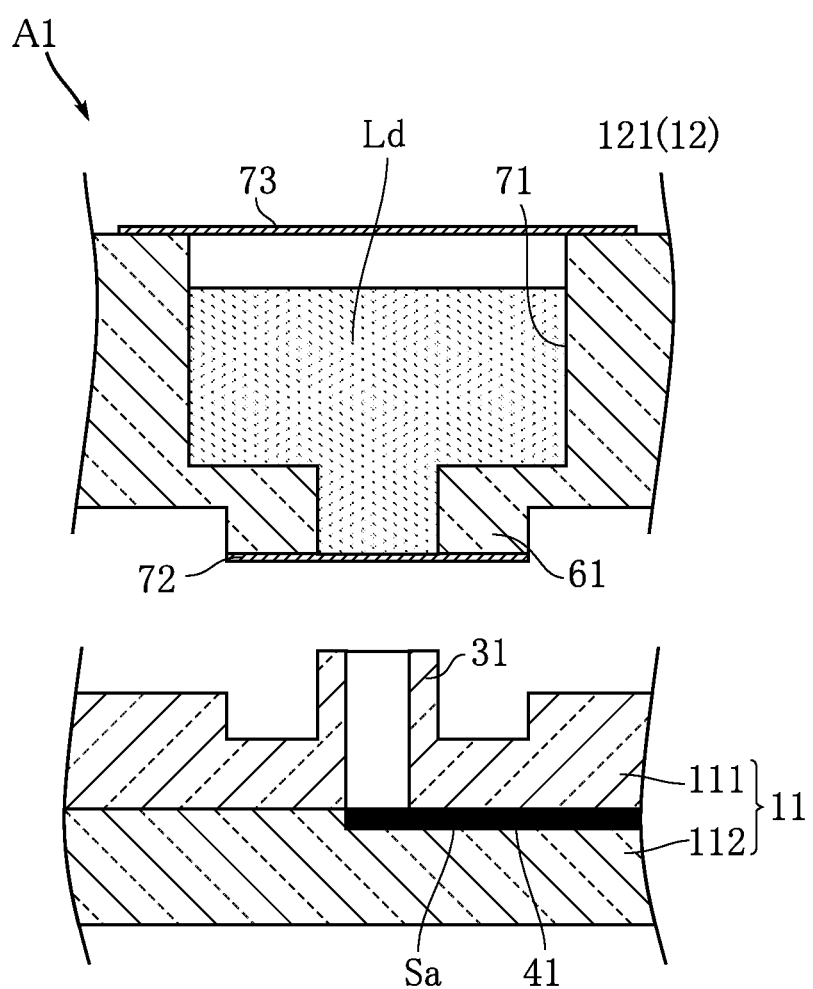
FIG. 3 is an enlarged sectional view showing a part of the analytical tool of FIG. 1 in a separated state.
Figure 4:
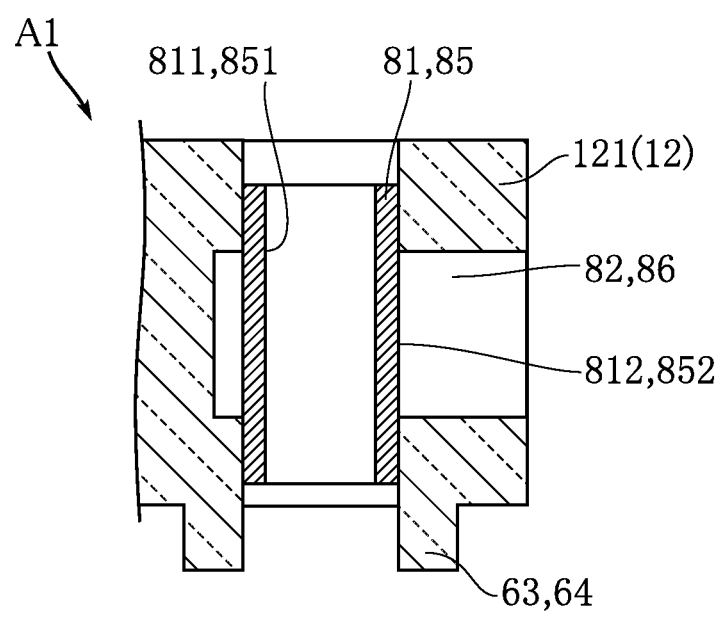
FIG. 4 is an enlarged sectional view showing a part of the analytical tool of FIG. 1 in a separated state.
Figure 4:
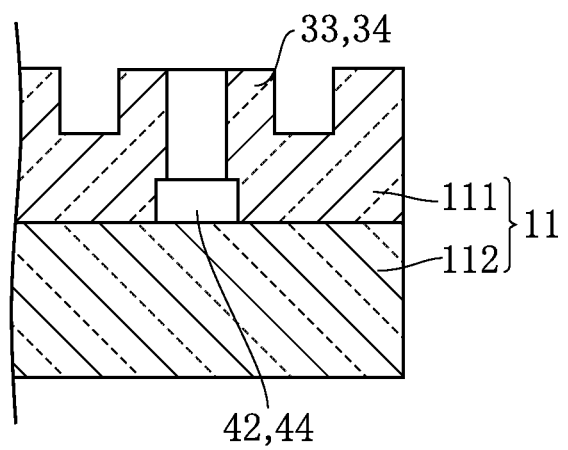
Figure 5:
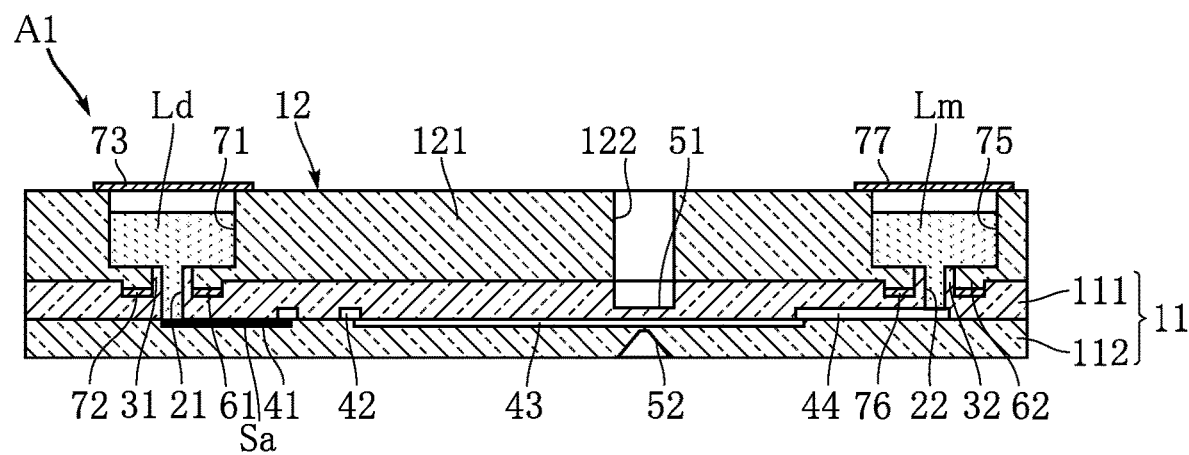
FIG. 5 is a sectional view of the analytical tool of FIG. 1 in a coupled state.
Figure 6:
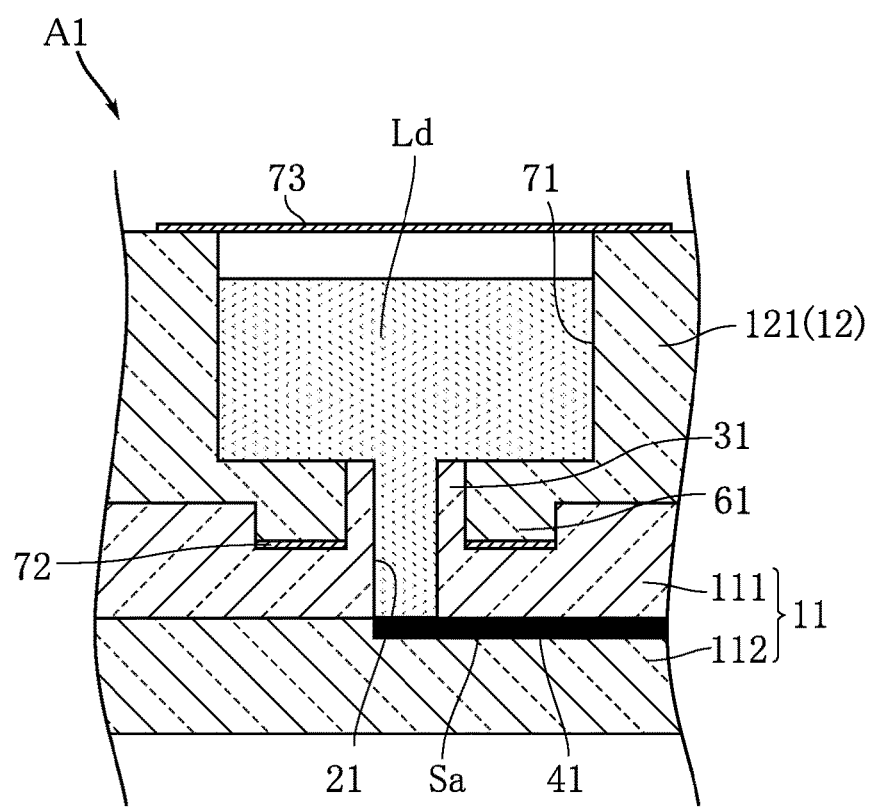
FIG. 6 is an enlarged sectional view showing a part of the analytical tool of FIG. 1 in a coupled state.
Figure 7:
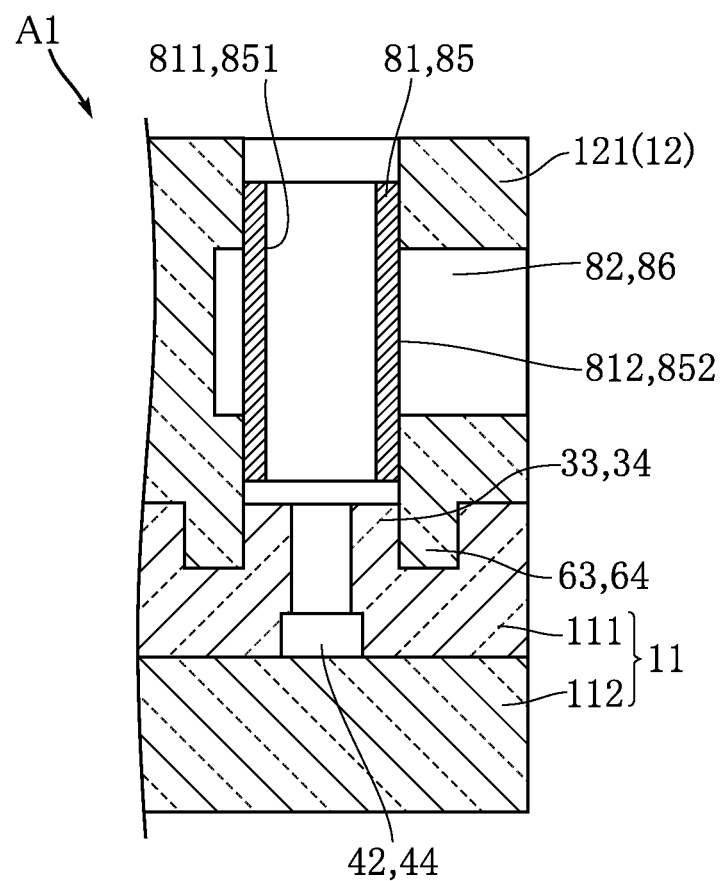
FIG. 7 is an enlarged sectional view showing a part of the analytical tool of FIG. 1 in a coupled state.

FIG. 1 is a schematic plan view of the analytical tool A1 in a separated state (see also FIG. 2). FIG. 2 is a sectional view taken along lines II-II in FIG. 1. FIG. 3 is an enlarged sectional view showing a part of the analytical tool A1 in a separated state. FIG. 4 is an enlarged sectional view showing a part of the analytical tool A1 in a separated state. FIG. 5 is a sectional view of the analytical tool A1 in a coupled state. FIG. 6 is an enlarged sectional view showing a part of the analytical tool A1 in a coupled state. FIG. 7 is an enlarged sectional view showing a part of the analytical tool A1 in a coupled state. In FIG. 1, illustration of a sealing member 73, a sealing member 77, diluent Ld and migration liquid Lm is omitted for easier understanding.

The analytical tool according to the present invention can be used, without limitation, for analyzing various kinds of samples by various analysis methods. Samples to be analyzed may be an analyte obtained from a living body (such as blood, urine or perspiration) or a natural substance (water, soil, etc.) for conducting environmental research such as water quality survey or geological survey. In the illustrated embodiment, which is presented merely as an example, the sample is human blood, and the blood is analyzed by electrophoresis for measuring hemoglobin in the blood.

Examples of the components contained in blood that can be measured by electrophoresis include hemoglobin (Hb), albumin (Alb), globulin ($\alpha 1$, $\alpha 2$, $\beta$, $\gamma$ globulin) and fibrinogen. Examples of hemoglobin include normal hemoglobin (HbA0), glycated hemoglobin, modified hemoglobin, fetal hemoglobin (HbF) and mutant hemoglobin. Examples of glycated hemoglobin include hemoglobin A1a (HbA1a), hemoglobin A1b (HbA1b), hemoglobin A1c (HbA1c) and GHbLys. Examples of hemoglobin A1c include stable HbA1c (s-HbA1c) and labile HbA1c (l-HbA1c). Examples of modified hemoglobin include carbamoylated Hb and acetylated Hb.

The analytical tool A1 includes a first unit 11 and a second unit 12, which are connectable to and separable from each other for bringing the analytical tool A1 into a coupled state or a separated state. FIGS. 2-4 show the analytical tool A1 in the separated state. FIGS. 5-7 show the analytical tool A1 in the coupled state.

The first unit 11 is made up of a first upper base 111 and a first lower base 112. The upper base 111 and the lower base 112, each being a plate generally in the form of an elongated rectangle, are bonded to each other. The upper base 111 and the lower base 112 may be made of glass, fused silica or plastic. Unlike the illustrated embodiment, the first unit 11 may be made up as a single member.

The first unit 11 includes connecting portions 31, 32, 33 and 34, a sample collecting portion 41, a guide passage 42, an analysis portion 43, a guide passage 44, a light-incident recess 51 and a light-exiting recess 52.

The connecting portions 31, 32, 33 and 34 are to be connected to corresponding portions of the second unit 12 to realize coupling of the first unit 11 and the second unit 12. As shown in FIGS. 2 and 4, in this embodiment, each of the connecting portion 31, 32, 33 and 34 is in the form of a projection extending upward in the figures and formed with a through-hole vertically penetrating the projection. In plan view (as shown in FIG. 1), the connecting portions 31, 32, 33 and 34 are arranged to correspond in position to a diluent reservoir 71, a migration liquid reservoir 75, an electroconductive member 81 and an electroconductive member 85, respectively.

The sample collecting portion 41 is a generally straight portion into which a predetermined amount of sample is introduced when the analytical tool A1 is in the separated state, and the sample is retained in the sample collecting portion 41 until the analytical tool A1 is brought into the coupled state. In this embodiment, the sample collecting portion 41 is a narrow passage connected, at one end (upstream end), to the connecting portion 31 and configured to retain a predetermined amount of sample introduced by capillary action.

The size of the sample collecting portion 41 is not limited to a particular one. As an example, the sample collecting portion 41 may be 100 to 1000 µm in width, 100 to 1000 µm in depth and 1 to 20 mm in length. For example, the amount of a sample that can be held in the sample collecting portion 41 may be 0.01 to 20 µL. In this embodiment, the sample collecting portion 41 is provided by a narrow groove formed in the lower base 112 with the upper side of the groove is covered with the upper base 111.

The guide passage 42 extends along a nonlinear path from the downstream end of the sample collecting portion 41 to the connecting portion 33 via the location of a first end (left end in FIG. 1) of the analysis portion 43. The guide passage 42 is provided for guiding a diluted sample Sm (obtained by diluting a sample Sa with a diluent Ld as described later) to the analysis portion 43 and the connecting portion 33. In this embodiment, the guide passage 42 includes a relatively long straight portion extending in the width direction (vertical direction in FIG. 1) perpendicular to the longitudinal direction of the analytical tool A1, and the above-mentioned first end of the analysis portion 43 is connected to this widthwise-extending portion in communication therewith. The guide passage 42 may be provided by a groove formed in the upper base 111 in a bent manner as depicted in the figure. The lower side of the groove is covered with the lower base 112.

The analysis portion 43 is an area where analysis is to be performed. In this embodiment utilizing electrophoresis, the analysis portion 43 serves as a capillary. The analysis portion 43 extends straight in the longitudinal direction of the analytical tool A1. While the first end of the analysis portion 43 is connected to the guide passage 42, the other or second end of the analysis portion 43 is connected to the guide passage 44 in communication therewith.

The size of the analysis portion 43 is not limited to a particular one. As an example, the analysis portion 43 may be 25 to 100 µm in width, 25 to 100 µm in depth and 5 to 150 mm in length. In this embodiment, the analysis portion 43 is provided by a narrow groove formed in the lower base 112. The upper side of the groove is covered with the upper base 111.

The guide passage 44 has a first end (right end in FIG. 1) connected to the connecting portion 32 (corresponding in position to the center of the migration liquid reservoir 75) and a second or opposite end connected to the connecting portion 34 (corresponding in position to the electroconductive member 85). An intermediate portion of the guide passage 44 between the first end and the second end is connected to the second end of the analysis portion 43. The guide passage 44 is provided for guiding a migration liquid Lm (described later) to the analysis portion 43 and also to the connecting portion 34. In this embodiment, the guide passage 44 is provided by a bent groove formed in the upper base 111. The lower side of the groove is covered by the lower base 112.

The light-incident recess 51 is a portion through which light is taken in when analysis by electrophoresis is performed. In this embodiment, the light-incident recess 51 is formed in the upper surface of the upper base 111 at a location overlapping with the analysis portion 43 in plan view. The light-incident recess 51 is generally cylindrical, for example.

The light-exiting recess 52 is a portion through which the above-mentioned light exits the analytical tool A1. In this embodiment, the light-exiting recess 52 is formed in the lower surface of the lower base 112 at a location overlapping with the analysis portion 43 in plan view such that the center of the light-exiting recess 52 coincides with the center of the light-incident recess 51. The light-exiting recess 52 is generally conical, for example.

The second unit 12 includes a second base 121. For example, the second base 121 is made of glass, fused silica or plastic. Unlike this embodiment, the second base 121 may be made up of more than one member.

The second unit 12 includes a through-hole 122, a diluent reservoir 71, a migration liquid reservoir 75, sealing members 72, 73, 76 and 77, cylindrical, electroconductive members or conductors 81, 85 and electrode-receiving recesses 82, 86.

The through-hole 122 penetrates the second base 121 in the thickness direction. The through-hole 122 overlaps with the light-incident recess 51 of the first unit 11 in plan view so that their combination forms a single (possibly cylindrical) space.

The diluent reservoir 71 is provided adjacent to a first end of the second unit 12 in the longitudinal direction. The diluent reservoir 71 is an example of a particular liquid reservoir which confines a diluent Ld as an example of particular liquid according to the present invention. In this embodiment, the diluent reservoir 71 is provided using a through-hole formed in the second base 121.

The diluent Ld is to be mixed with a sample Sa to form a diluted sample Sm. The main component of the diluent Ld is not limited to a particular one and may be water or saline, for example. Preferably, use may be made of a liquid containing a component similar to that of the migration liquid Lm. The diluent Ld may contain a cationic group-containing compound added to the main component. For example, the cationic group-containing compound may be cationic group-containing polysaccharide. For example, the cationic group-containing polysaccharide may be at least one polysaccharide selected from the group consisting of sulfated polysaccharide, carboxylated polysaccharide, sulfonated polysaccharide and phosphorylated polysaccharide. Preferably, the carboxylated polysaccharide may be alginic acid or its salt (for example, sodium alginate). For example, the sulfated polysaccharides may be chondroitin sulfate. Chondroitin sulfate has seven types: A, B, C, D, E, H and K, and any of these types may be used. The cationic group-containing compound (e.g. chondroitin sulfate) may be contained in a concentration of 0.01 to 5% by weight.

The diluent reservoir 71 is sealed with two sealing members 72 and 73. Each of the sealing members 72 and 73 is attached to the surface of the second base 121 by using an adhesive, for example, so that the sealing condition is to be maintained. Each of the sealing member 72, 73 is not limited to a particular configuration, and a plate or a film may be employed. In the illustrated embodiment, each sealing member 72, 73 is a film. For example, the film may be a laminated film formed by laminating a resin layer and an aluminum layer.

The connecting portion 61 is provided under the diluent reservoir 71 for connection with the connecting portion 31 of the first unit 11. In this embodiment, the connecting portion 61 is in the form of a projection extending downward (see FIGS. 2 and 3) and is formed with a through-hole vertically penetrating the projection. In this embodiment, the sealing member 72 is attached to the lower end of the connecting portion 61.

The migration liquid reservoir 75 is provided adjacent to the second end (right end in FIG. 2) of the second unit 12. The migration liquid reservoir 75 is configured to hold a migration liquid Lm (which may often be referred to as "buffer solution"). In this embodiment, the migration liquid reservoir 75 is provided by a through-hole formed in the second base 121.

To conduct an analysis by electrophoresis, the migration liquid Lm is introduced into the analysis portion 43 for causing electroosmotic flow. The migration liquid Lm is not limited to a particular kind, but preferably one that contains acid. Examples of acid are citric acid, maleic acid, tartaric acid, succinic acid, fumaric acid, phthalic acid, malonic acid and malic acid. Preferably, the migration liquid Lm may contain a weak base. Examples of weak base are arginine, lysine, histidine, and Tris or tris(hydroxymethyl)aminomethane. For example, the pH of the migration liquid Lm may be in the range of 4.5 to 6. Examples of buffer used for the migration liquid Lm are MES, ADA, ACES, BES, MOPS, TES and HEPES. The migration liquid Lm may also contain a cationic group-containing compound mentioned above with respect to the diluent Ld. For example, the cationic group-containing compound (e.g. chondroitin sulfate) may be contained in a concentration of 0.01 to 5% by weight.

The migration liquid reservoir 75 is sealed with two sealing members 76 and 77. Each of the sealing members 76, 77 is attached to the surface of the second base 121 by using an adhesive, for example, so that the sealing condition is to be maintained. Each sealing member 76, 77 is not limited to a particular configuration, and a plate or a film may be employed. In this embodiment, each of the sealing member 76, 77 is a film. For example, the film may be a laminated film formed by laminating a resin layer and an aluminum layer.

The connecting portion 62 is provided under the migration liquid reservoir 75 for connection with the connecting portion 32 of the first unit 11. In this embodiment, the connecting portion 62 is in the form of a projection extending downward and is formed with a through-hole vertically penetrating the projection. In this embodiment, the sealing member 76 is attached to the lower end of the connecting portion 62.

As understood from FIGS. 1 and 4, the cylindrical conductors 81 and 85 are generally identical in structure. Similarly, the electrode-receiving recesses 82 and 86 are generally identical in structure, and so are the connecting portions 63 and 64. Thus, only one of the respective pairs, i.e., the cylindrical conductor 81, the electrode-receiving recess 82 and the connecting portion 63 are described below.

The cylindrical conductor 81 is disposed within a through-hole penetrating the second base 121 in the thickness direction. The cylindrical conductor 81 is made of an electrically conductive material such as metal. The cylindrical conductor 81 in the illustrated embodiment has an annular cross section. The present invention, however, is not limited to this, and the cylindrical conductor 81 may have a different cross section.

The electrode-receiving recess 82 is formed in one of the two side surfaces of the second base 121 that are opposite to each other in the width direction. As shown in FIG. 4, the cylindrical conductor 81 has an intermediate portion and two end portions flaking the intermediate portion in the longitudinal direction of the conductor 81. Specifically, the intermediate portion is housed in the electrode-receiving recess 82, and the end portions are located within the second base 121 but not housed in the electrode-receiving recess 82. The shape of the electrode-receiving recess 82 is not limited to a particular one. In this embodiment, the electrode-receiving recess 82 is triangular in plan view.

The cylindrical conductor 81 has an inner surface and an outer surface 812. The inner surface defines a voltage application passage 811 used for applying voltage to a diluted sample Sm flowing through the passage. The outer surface 812 has a part that is exposed to the outside through the electrode-receiving recess 82.

The connecting portion 63 is provided for connection with the connecting portion 33 of the first unit 11. In this embodiment, the connecting portion 63 is in the form of a projection extending downward in the figure and is formed with a through-hole.

FIGS. 2 and 3 show the sample Sa collected and held in the sample collecting portion 41 while the first unit 11 and the second unit 12 are separate from each other. The collection of the sample Sa may be conducted by dripping human blood to the end of the sample collecting portion 41 using a dropper (not shown) for example. Alternatively, the collection may be conducted by direct application of blood from a punctured finger, for example, to the end of the sample collecting portion 41. As described above, the sample collecting portion 41 is configured as a narrow passage for capillary action, and thus a predetermined amount of sample Sa is automatically drawn into the sample collecting portion 41. Thereafter, the collected sample Sa remains within the sample collecting portion 41.

FIGS. 5-7 show the first unit 11 and the second unit 12 coupled together after the sample Sa is applied to the sample collecting portion 41. As shown in FIG. 5, the first unit 11 and the second unit 12 coupled together form an integral piece of analytical tool A1 having an elongated shape. As shown in FIG. 6, the connecting portion 31 of the first unit 11 is connected with the connecting portion 61 of the second unit 12. In this connection, the connecting portion 31 breaks the sealing member 72 attached to the lower surface of the connecting portion 61 and is inserted into the through-hole of the connecting portion 61. The through-hole in the connecting portion 31 forms a fluid passage 21 for the flow of the diluent Ld from the diluent reservoir 71 into the sample collecting portion 41. In this way, as the first unit 11 and the second unit 12 are coupled, the sealing member 72 is broken and the fluid passage 21 is formed. In this embodiment, the fluid passage 21 is defined solely by the connecting portion 31, which is a part of the first unit 11.

The coupling of the first unit 11 and the second unit 12 provides substantially the same effect to the system involving the migration liquid reservoir 75, the sealing member 76, the connecting portion 32 and the connecting portion 62. Specifically, when the first unit 11 and the second unit 12 are coupled, the sealing member 76 is broken, and a fluid passage 22 is formed for allowing the migration liquid Lm to flow into the first unit 11. In the illustrated embodiment, the fluid passage 22 is defined solely by the connecting portion 32, which is a part of the first unit 11.

Also, as shown in FIG. 7, the connecting portions 33, 34 of the first unit 11 are connected to the connecting portions 63, 64 of the second unit 12. As a result, the voltage application passages 811, 851 of the cylindrical conductors 81, 85 are connected to the guide passages 42, 44 of the first unit 11. The upper end of the voltage application passages 811, 851 are left open or connected to appropriate portions of an analytical device B, which will be described later.

Figure 8:
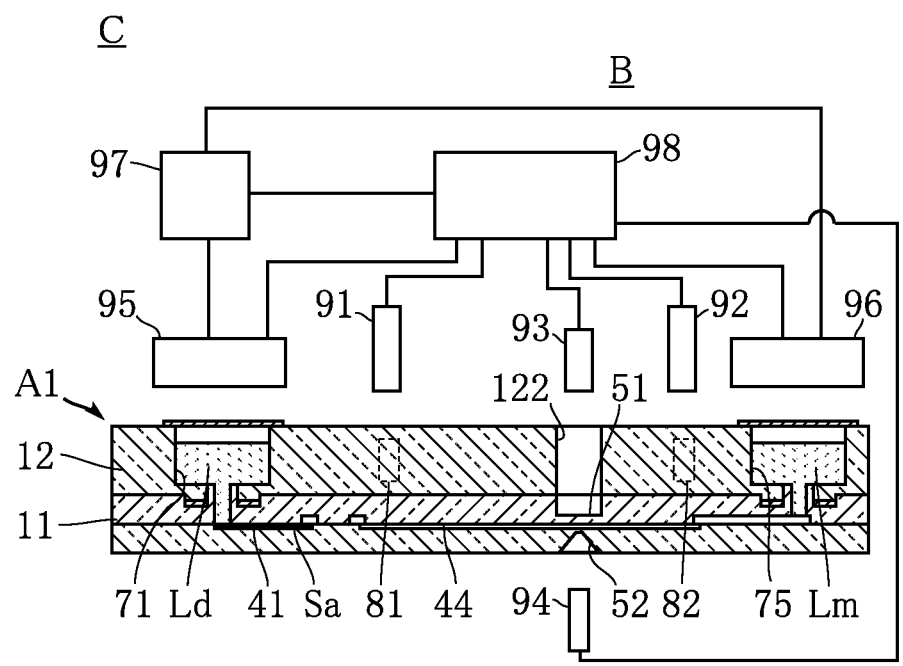
FIG. 8 is a schematic view of an analytical system according to a first embodiment of the present invention.

FIG. 8 shows an analytical system using the analytical tool A1, according to an aspect of the present invention. The illustrated analytical system C includes the above-described analytical tool A1 and an analytical device B.

The analytical device B is configured to perform analysis by electrophoresis, with the analytical tool A1 mounted to the device. The analytical device B includes electrodes 91 and 92, a light-emitting unit 93, a light-receiving unit 94, pressure nozzles 95 and 96, a pump 97 and a control unit 98.

The electrodes 91 and 92 are provided for applying a voltage to the analysis portion 43 as a capillary tube in analysis by electrophoresis. The electrode 91 is brought into contact with the outer surface 812 of the cylindrical conductor 81 of the analytical tool A1 to apply a voltage. The electrode 92 is brought into contact with the outer surface 852 of the cylindrical conductor 85 of the analytical tool A1 to apply a voltage. The voltage applied across the electrodes 91 and 92 is not limited to a particular value and may be 0.5 to 20 kV, for example. In FIG. 8, the arrangement of the electrodes 91 and 92 is illustrated schematically. In practice, the electrodes 91 and 92 are moved toward or away from the analytical tool A1 in the width direction.

The light-emitting unit 93 emits light for measuring absorbance in analysis by electrophoresis. The light-emitting unit 93 includes a light-emitting element such as an LED chip for emitting light in a predetermined wavelength range, an optical filter and a lens. The optical filter passes light of certain wavelengths among the light from the light-emitting element, while attenuating light of other wavelengths. The light passing through the optical filter is focused by the lens onto a predetermined spot in the analysis portion 43 of the analytical tool A1. The light-emitting unit 93 may further include at least one slit for removing an undesired component of light which may cause scattering among the light having passed through the optical filter and the lens.

The light-receiving unit 94 receives light passing through the analysis portion 43 of the analytical tool A1. For example, the light-receiving unit 94 includes a photodiode or photo IC.

The pressure nozzle 95 is configured to come into close contact with the diluent reservoir 71 of the analytical tool A1 to apply a predetermined pressure (positive pressure or negative pressure) to the diluent reservoir 71. The pressure nozzle 95 may be provided with a means for breaking the sealing member 73 of the analytical tool A1. Alternatively, the analytical device B may include a means for breaking the sealing member 73 separately from the pressure nozzle 95.

The pressure nozzle 96 is configured to come into close contact with the migration liquid reservoir 75 of the analytical tool A1 to apply a predetermined pressure (positive pressure or negative pressure) to the migration liquid reservoir 75. The pressure nozzle 96 may be provided with a means for breaking the sealing member 77 of the analytical tool A1. Alternatively, the analytical device B may include a means for breaking the sealing member 77 separately from the pressure nozzle 96.

The pump 97 is connected to the pressure nozzles 95 and 96. The pump 97 serves as a pressure source for enabling pressure application by the pressure nozzles 95 and 96. The pump 97 may be connected to an additional pressure nozzle (not shown) other than the pressure nozzles 95 and 96 for applying pressure with respect to another portion of the analytical tool A1.

The control unit 98 controls various units of the analytical device B. The control unit 98 includes a CPU, a memory and an interface, for example.

The analysis process using the analytical system C according to an aspect of the present invention is described below. This analysis process may include a sample collection step, a migration liquid introduction step, a mixing step and an electrophoresis step.

<Sample Collection Step>

First, a sample Sa is prepared. In this embodiment, the sample Sa is blood collected from a human body. The blood may be whole blood or blood after hemolysis. As shown in FIG. 2, a predetermined amount of sample Sa is drawn into the sample collecting portion 41 of the analytical tool A1 in a separated state by capillary action. Then, the analytical tool A1 is brought into the coupled state as shown in FIGS. 5-7. In this process, the sealing members 72 and 76 are broken, and fluid passages 21 and 22 are formed. The analytical tool A1 in the coupled state is then mounted to the analytical device B, as schematically shown in FIG. 8.

<Migration Liquid Introducing Process>

Figure 9:
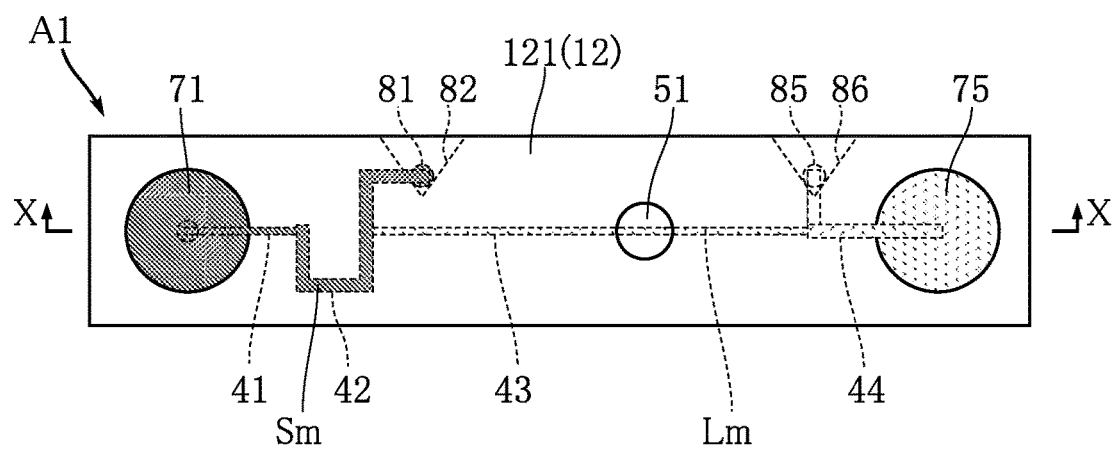
FIG. 9 is a schematic plan view showing the state prepared for analysis.
Figure 10:
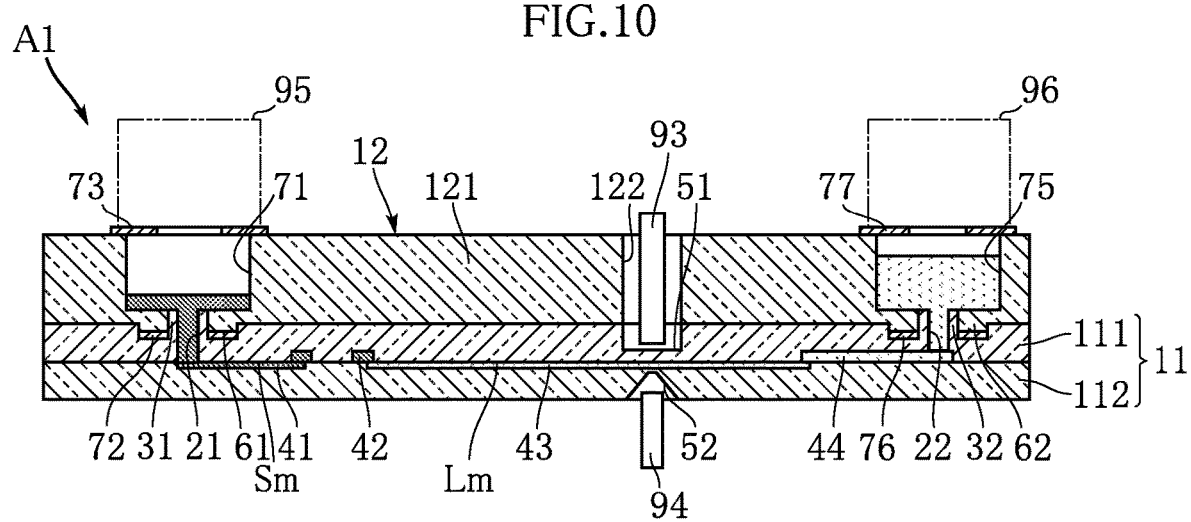
FIG. 10 is a schematic sectional view taken along lines X-X in FIG. 9.

Then, the migration liquid Lm is introduced into the analysis portion 43. Specifically, as shown in FIGS. 9 and 10, with the fluid passage 22 formed in the analytical tool A1, a positive pressure is applied from the pressure nozzle 96 to the migration liquid reservoir 75 through the broken sealing member 77. As a result, the migration liquid Lm in the migration liquid reservoir 75 flows through the fluid passage 22 into the guide passage 44 and then into the analysis portion 43 in the first unit 11.

<Mixing Step>

Then, the sample Sa is mixed with the diluent Ld. Specifically, as shown in FIGS. 9 and 10, with the fluid passage 21 formed in the analytical tool A1, a positive pressure is applied from the pressure nozzle 95 to the diluent reservoir 71 through the broken sealing member 73. As a result, the diluent Ld in the diluent reservoir 71 flows through the fluid passage 21 into the sample collecting portion 41 of the first unit 11. Since the predetermined amount of sample Sa is present in the sample collecting portion 41, the diluent Ld flowing into the sample collecting portion 41 mixes with the sample Sa. Thus, the sample Sa is diluted with the diluent Ld, whereby diluted sample Sm is obtained. The diluted sample Sm is introduced into the guide passage 42 due to the positive pressure from the pressure nozzle 95. The diluted sample Sm introduced into the guide passage 42 reaches the cylindrical conductor 81 through the connecting portion 33. For mixing the sample Sa and the diluent Ld, use may be made of other techniques. For example, a positive pressure and a negative pressure may be alternately applied from the pressure nozzle 95 to cause reciprocating flow in the sample collecting portion 41 and the guide passage 42. Alternatively, a mixing reservoir for mixing the sample Sa and the diluent Ld may be provided between the sample collecting portion 41 and the first end of the analysis portion 43.

<Electrophoresis Step>

Figure 11:
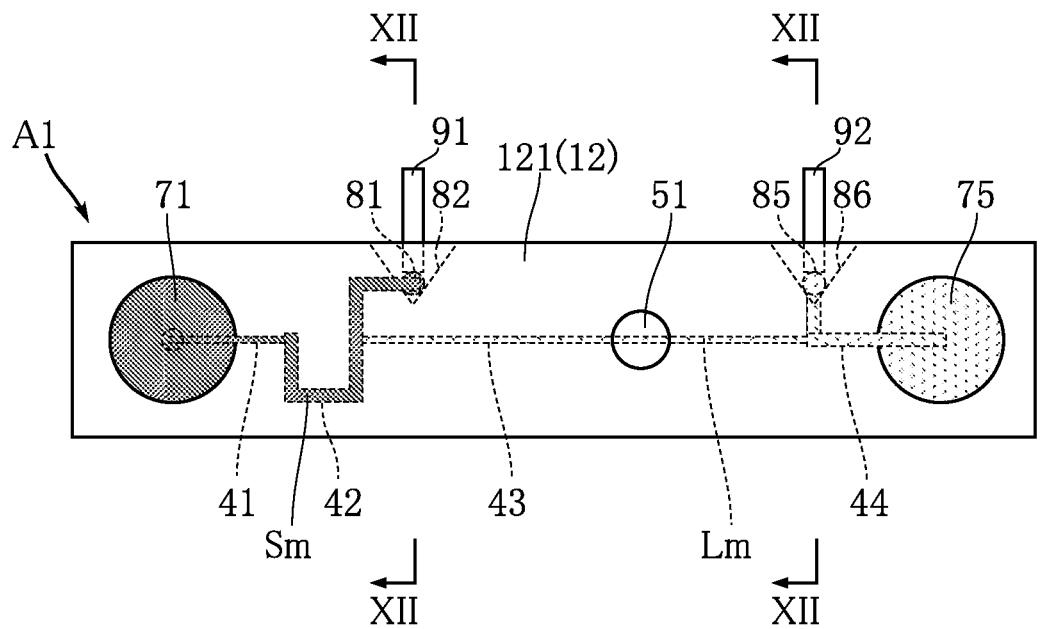
FIG. 11 is a schematic plan view showing the analysis step.
Figure 12:
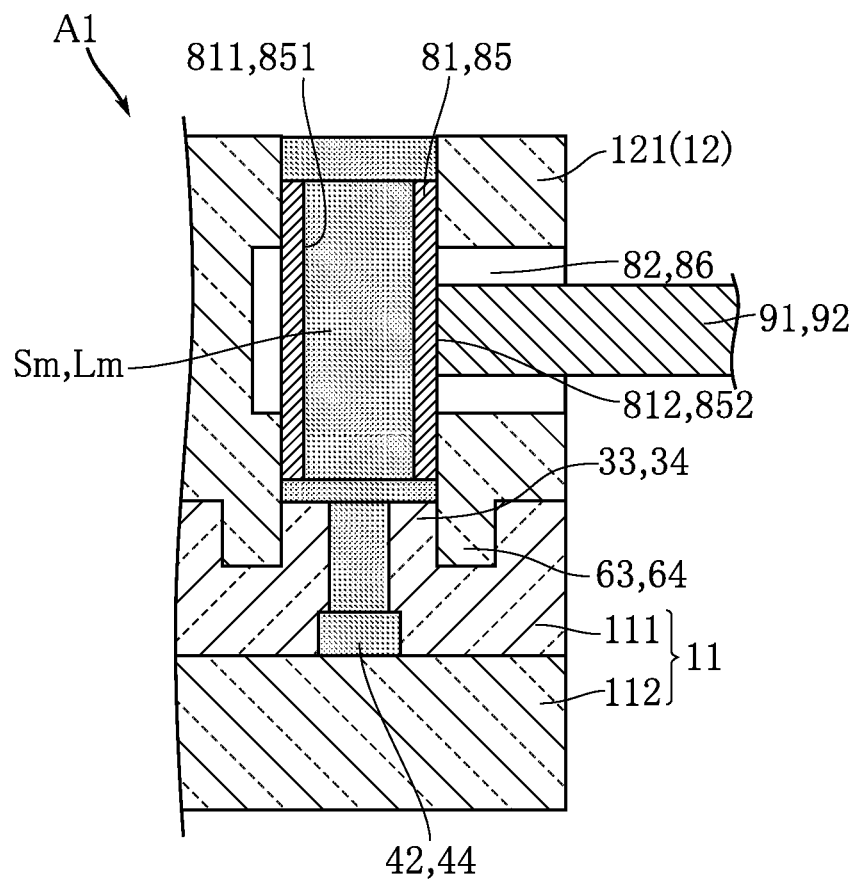
FIG. 12 is a schematic sectional view taken along lines XII-XII in FIG. 11.

Then, as shown in FIGS. 11 and 12, the electrode 91 is brought into contact with the cylindrical conductor 81, and the electrode 92 is brought into contact with the cylindrical conductor 85. Then, a voltage is applied across the cylindrical conductor 81 and the cylindrical conductor 85 under the control by the control unit 98. For example, the voltage may be in the range of 0.5 to 20 kV. The voltage application causes electroosmotic flow to gradually move the diluted sample Sm through the analysis portion 43. Since the guide passage 42 is filled with the diluted sample Sm, electrophoresis occurs with the diluted sample Sm being continuously supplied to the analysis portion 43. Meanwhile, light is emitted from the light-emitting unit 93 for measuring absorbance with the light-receiving unit 94. The relationship between the absorbance and the time elapsed from the start of the voltage application across the electrodes 91 and 92 is monitored. The absorbance peak corresponding to a component in the diluted sample Sm which moves at a relatively high speed appears after the lapse of a relatively short time from the start of the voltage application. On the other hand, the absorbance peak corresponding to a component in the diluted sample Sm which moves at a relatively low speed appears after the lapse of a relatively long time from the start of the voltage application. Based on these phenomena, the analysis (separation measurement) of the components contained in the diluted sample Sm is performed. The measured absorbance may then be subjected to computation (such as differential or finite differences processing by the control unit 98) to form electropherogram. The peak height or the peak area in the electropherogram may be computed, whereby the composition or the like of the diluted sample Sm is determined. In this way, the analysis of the sample Sa (diluted sample Sm) is completed.

The advantages of the analytical tool A1 and the analytical device B are described below.

According to the embodiment, as shown in FIGS. 3 and 6, the fluid passage 21 is formed when the analytical tool A1 in the separated state is brought into the coupled state. The fluid passage 21 is defined solely by the connecting portion 31, which is a part of the first unit 11. In this way, the analytical tool A1 of this embodiment allows the diluent Ld stored as a particular liquid in the second unit 12 to be introduced into the first unit 11 without using any other tool. Thus, the analytical device B does not need to include a nozzle or the like for dispensing the diluent Ld. When the diluent Ld is introduced from the second unit 12 into the first unit 11 for conducting analysis, the analytical device B does not come into contact with the diluent Ld. Thus, the analytical device B is not contaminated. Moreover, containers such as a bottle for storing the diluent Ld and the migration liquid Lm are not necessary, which leads to reduction in size and manufacturing cost of the system. Furthermore, since it is not necessary to store the amount of diluent Ld or migration liquid Lm that allows plural times of measurement, the cost for a single time of analysis reduces.

Breakage of the sealing member 72 and formation of the fluid passage 21 are achieved simultaneously just by coupling the first unit 11 and the second unit 12. Thus, the diluent Ld, which has been properly confined in the diluent reservoir 71, is quickly introduced into the sample collecting portion 41 of first unit 11 without the need for using an additional means for breaking the sealing member 72. The same advantage holds for the breakage of the sealing member 76 of the migration liquid reservoir 75.

Since the analytical tool A1 is designed as a disposable type for use in analysis by electrophoresis, the second unit 12 merely needs to store the amount of diluent Ld and migration liquid Lm necessary for a single time of analysis. Moreover, analysis by electrophoresis does not require liquid or reagent other than diluent Ld or migration liquid Lm.

The collection of the sample Sa by utilizing capillary action allows a predetermined amount of sample Sa to be precisely introduced into the sample collecting portion 41. Moreover, the analytical tool A1 for use in analysis by electrophoresis is formed with an analysis portion 43 as a capillary tube. The analysis portion 43, which is a narrow passage, can be formed by the process similar to that for forming the sample collecting portion 41.

Voltage is applied from the electrode 91 brought into contact with the outer surface 812 of the cylindrical conductor 81 to the voltage application passage 811 defined by the inner surface of the cylindrical conductor 81. Thus, the electrode 91, which is an end member for voltage application of the analytical device B, does not come into contact with the diluted sample Sm or the like. This eliminates the need for cleaning or replacing the electrode 91 after each time of analysis. In this way, contamination of the analytical device B is avoided, so that a plurality of times of analysis can be performed efficiently. This advantage holds for the electrode 92 coming into contact with the cylindrical conductor 85.

FIGS. 13-16 show other embodiments of the present invention. In these figures, the elements that are identical or similar to those of the foregoing embodiment are designated by the same reference signs as those used for the foregoing embodiment.

Figure 13:
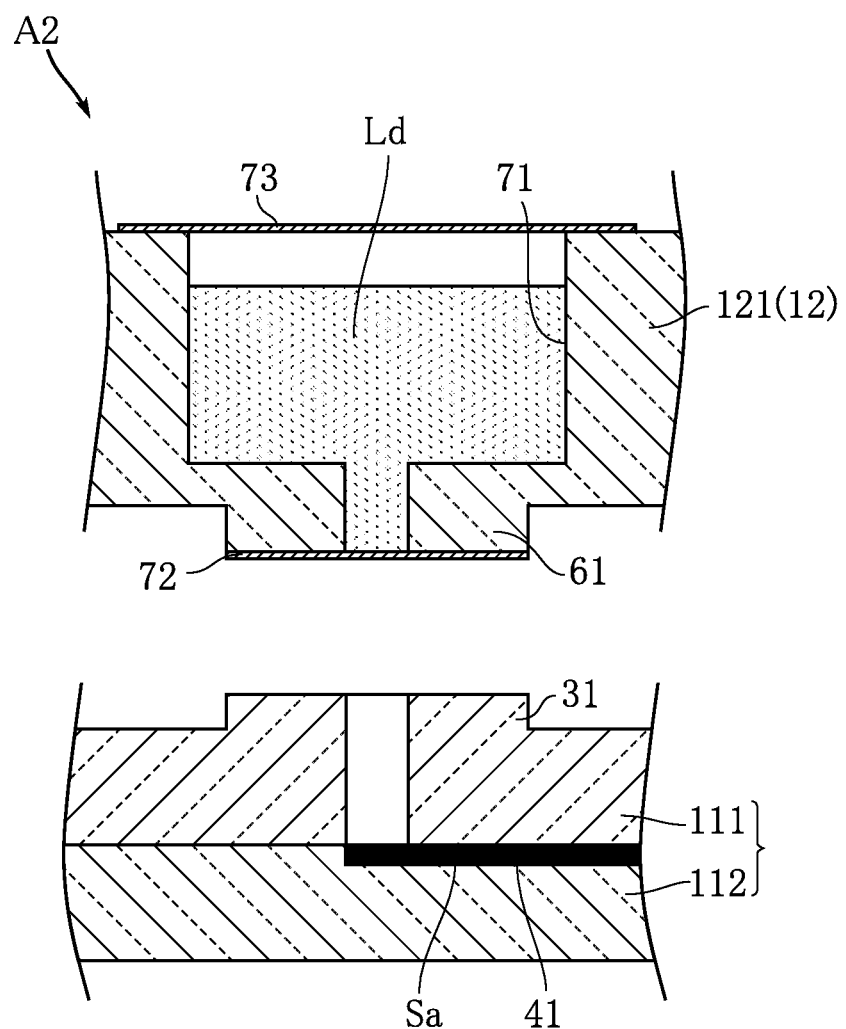
FIG. 13 is an enlarged sectional view showing a part of an analytical tool in a separated state, according to a second embodiment of the present invention.
Figure 14:
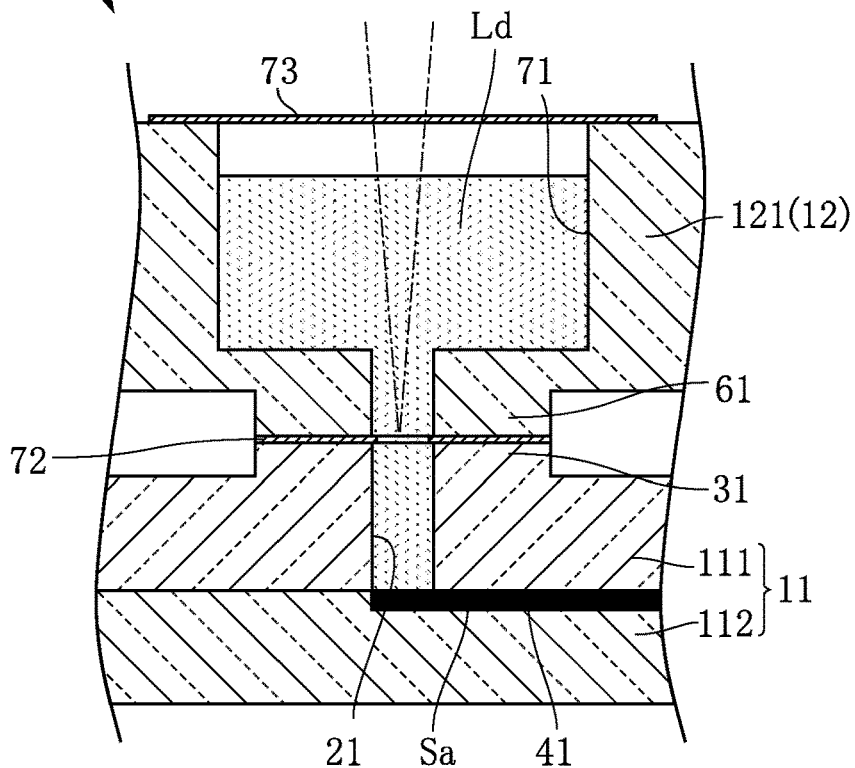
FIG. 14 is an enlarged sectional view showing a part of the analytical tool of FIG. 13 in a coupled state.

FIGS. 13 and 14 show an analytical tool according to another embodiment of the present invention. The analytical tool A2 of this embodiment differs from that of the foregoing embodiment in structure of the fluid passage 21 and connecting portions 31 and 61. FIG. 13 shows the analytical tool A2 in the separated state, and FIG. 14 shows the analytical tool A2 in the coupled state. In this embodiment, the through-holes formed in the connecting portion 31 and that formed in the connecting portion 61 are equal in diameter. In the coupled state shown in FIG. 14, the connecting portion 31 and the connecting portion 61 are pressed against each other via the sealing member 72. The sealing member 72 is broken by a breaking means such as a laser irradiation device which may be provided in the analytical device B. As a result, the fluid passage 21 is formed by the through-hole of the connecting portion 31 and the through-hole of the connecting portion 61. In this way, the fluid passage 21 is defined by the connecting portion 31, which is a part of the first unit 11, and the connecting portion 61, which is a part of the second unit 12.

This embodiment also allows proper analysis while preventing the analytical device B from having a complicated structure or being contaminated.

Figure 15:
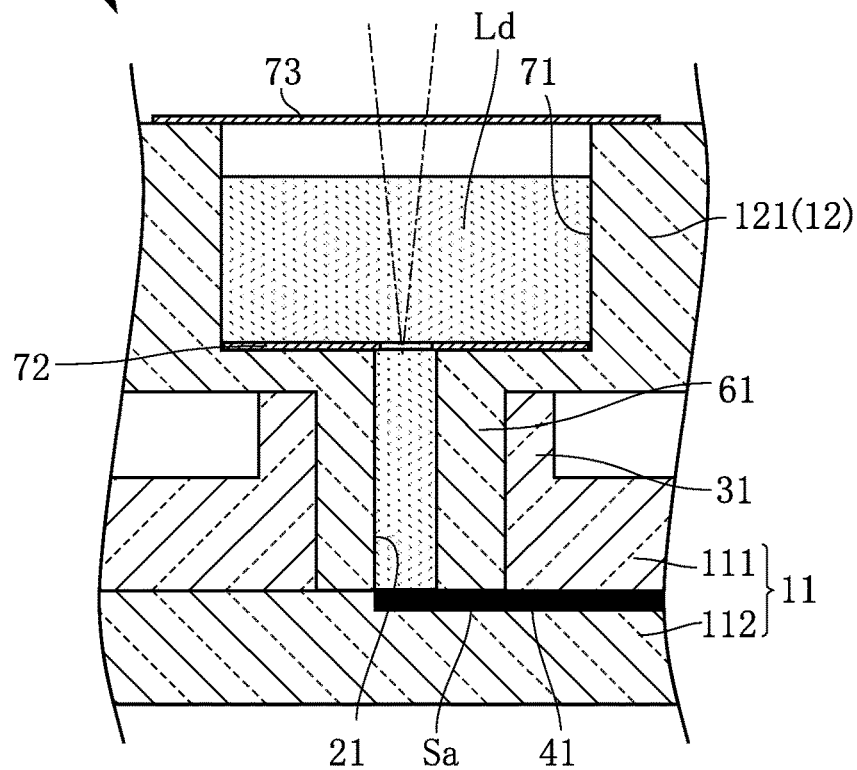
FIG. 15 is an enlarged sectional view showing a part of an analytical tool in a coupled state, according to a third embodiment of the present invention.

FIG. 15 shows an analytical tool according to another embodiment of the present invention. In the coupled state of the analytical tool A3 of this embodiment, the connecting portion 61 is inserted into the through-hole of the connecting portion 31. The sealing member 72 is attached to the diluent reservoir 71 above the connecting portion 61. When the sealing member 72 is broken by, for example, the above-described laser irradiation device, the fluid passage 21 is formed by the through-hole of the connecting portion 61. In this way, according to this embodiment, the fluid passage 21 is defined solely by the connecting portion 61, which is a part of the second unit 12.

This embodiment also allows proper analysis while preventing the analytical device B from having a complicated structure or being contaminated.

Figure 16:
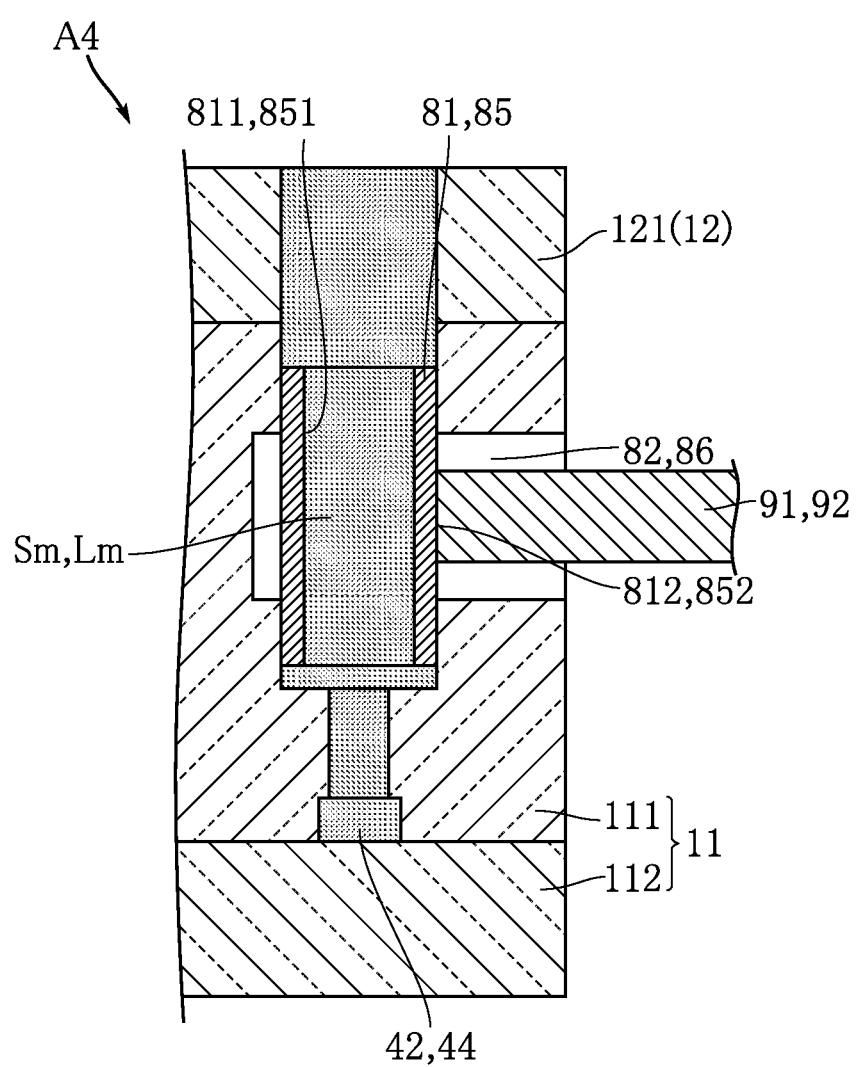
FIG. 16 is an enlarged sectional view showing a part of an analytical tool according to a fourth embodiment of the present invention.

FIG. 16 shows an analytical tool according to another embodiment of the present invention. The analytical tool A4 of this embodiment differs from the analytical tool A1 in structure of the cylindrical conductors 81 and 85. In this embodiment, the cylindrical conductors 81 and 85 are provided in the first unit 11. Accordingly, the electrode-receiving recesses 82 and 86 for receiving the cylindrical conductors 81 and 85 are also formed in the first unit 11. The first unit 11 has two openings above the cylindrical conductors 81 and 85, respectively, and each opening is connected to a corresponding one of the through-holes (passages) formed in the second unit 12.

This embodiment also allows proper analysis while preventing the analytical device B from having a complicated structure or being contaminated.

The analytical tool and analytical system according to the present invention are not limited to foregoing embodiments. The structure of each part of the analytical tool and analytical system according to the present invention can be varied in design in many ways.

The invention claimed is:

1. An analytical tool, comprising:
   a first unit including an analysis portion for analyzing a sample, and a connecting portion having a projection: and
   a second unit configured to be coupled with the first unit, and including a liquid reservoir for confining a particular liquid used for analyzing the sample and configured to be connected to the connecting portion,
   wherein the second unit includes a sealing member that seals the liquid reservoir, and wherein the tool is configured such that, when the second unit is connected to the connecting portion, the projection breaks the sealing member, and the fluid passage is formed,
   wherein the tool is configured such that a fluid passage for conducting the particular liquid from the liquid reservoir into the first unit is formed in the analytical tool when the first unit and the second unit are coupled.

2. The analytical tool according to claim 1, wherein the first unit includes a sample collecting portion for taking the sample in.

3. The analytical tool according to claim 2, wherein the sample is moved in the sample collecting portion by capillary action.

4. The analytical tool according to claim 1, wherein the analytical tool is configured as a disposable tool.

5. The analytical tool according to claim 1, wherein the analytical tool is configured for use in analysis by electrophoresis, and the analysis portion comprises a capillary tube.

6. The analytical tool according to claim 5, further comprising a cylindrical electroconductive member having an inner surface and an outer surface, the inner surface defining a voltage application passage, the outer surface being exposed to an outside.

7. The analytical tool according to claim 6, wherein the cylindrical electroconductive member is provided in the second unit.

8. An analytical system comprising:
   an analytical tool of claim 1; and
   an analytical device to which the analytical tool is mounted.

9. The analytical system according to claim 8, wherein the analytical device is configured to perform pressure control for realizing liquid flow relative to the fluid passage.

* * * * *